(12) United States Patent
Fainstain

(10) Patent No.: US 10,926,056 B2
(45) Date of Patent: Feb. 23, 2021

(54) METHOD, APPARATUS AND SYSTEM FOR MITIGATING MOTION SICKNESS IN A VIRTUAL REALITY ENVIRONMENT

(71) Applicant: Advanced Micro Devices, Inc., Santa Clara, CA (US)

(72) Inventor: Evgene Fainstain, Santa Clara, CA (US)

(73) Assignee: Advanced Micro Devices, Inc., Santa Clara, CA (US)

(*) Notice: Subject to any disclaimer, the term of this patent is extended or adjusted under 35 U.S.C. 154(b) by 0 days.

(21) Appl. No.: 15/840,310

(22) Filed: Dec. 13, 2017

(65) Prior Publication Data

US 2019/0076618 A1   Mar. 14, 2019

Related U.S. Application Data

(60) Provisional application No. 62/558,620, filed on Sep. 14, 2017.

(51) Int. Cl.
*A61M 21/00* (2006.01)
*G06F 3/01* (2006.01)
*G06T 11/60* (2006.01)

(52) U.S. Cl.
CPC ........... *A61M 21/00* (2013.01); *G06F 3/011* (2013.01); *G06F 3/016* (2013.01); *G06T 11/60* (2013.01); *A61M 2021/005* (2013.01); *A61M 2021/0022* (2013.01); *A61M 2205/3344* (2013.01); *A61M 2205/502* (2013.01); *A61M 2230/63* (2013.01); *G06F 2203/011* (2013.01); *G06F 2203/012* (2013.01)

(58) Field of Classification Search
CPC ................. G06F 3/016; A61M 21/00
USPC ........................................... 345/649
See application file for complete search history.

(56) References Cited

U.S. PATENT DOCUMENTS

| | | | |
|---|---|---|---|
| 8,817,087 B2 * | 8/2014 | Weng ................. | G01C 21/3664 345/683 |
| 2002/0089506 A1 * | 7/2002 | Templeman ............ | G06F 3/011 345/473 |
| 2005/0119812 A1 * | 6/2005 | Marchthaler ..... | B60R 21/01516 701/45 |
| 2016/0054837 A1 * | 2/2016 | Stafford ................ | A63F 13/825 563/33 |
| 2017/0271962 A1 * | 9/2017 | Wang ..................... | H02K 11/21 |

(Continued)

Primary Examiner — Hai Tao Sun
(74) Attorney, Agent, or Firm — Volpe Koenig

(57) ABSTRACT

Described herein are a method, system and apparatus for mitigating motion sickness in a virtual reality (VR) environment. In an implementation, the system and apparatus can include a VR controller board, a processor and a VR headset. In an implementation, the processor and VR headset are an integrated device. In general, the method includes capturing measurements using the VR controller board. The measurements are indicative of user directional movements in a physical environment relative to the VR environment. In an implementation, the measurements relate to changes in the location of the center of mass of the user relative to the VR controller board. The processor uses the measurements to determine predetermined actions in the VR environment. The predetermined actions are then executed in the VR environment nearly simultaneous with the user directional movements in the physical environment.

20 Claims, 7 Drawing Sheets

(56) References Cited

U.S. PATENT DOCUMENTS

2018/0089901 A1* 3/2018 Rober .................. G06T 19/006
2018/0113506 A1* 4/2018 Hall ....................... G06F 3/012
2018/0136816 A1* 5/2018 Tao ..................... G06F 3/04815

* cited by examiner

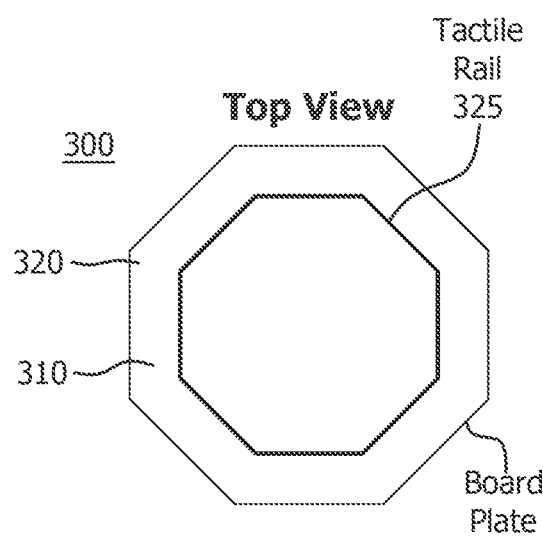
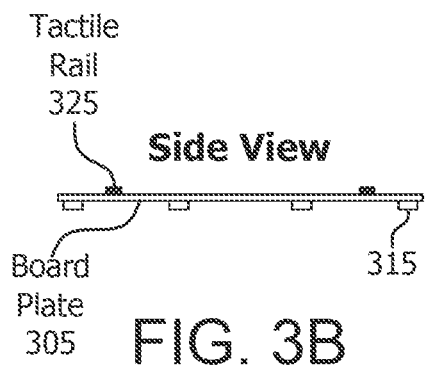
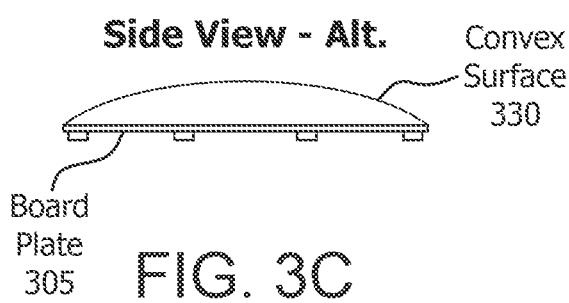
FIG. 3A
FIG. 3B
FIG. 3C
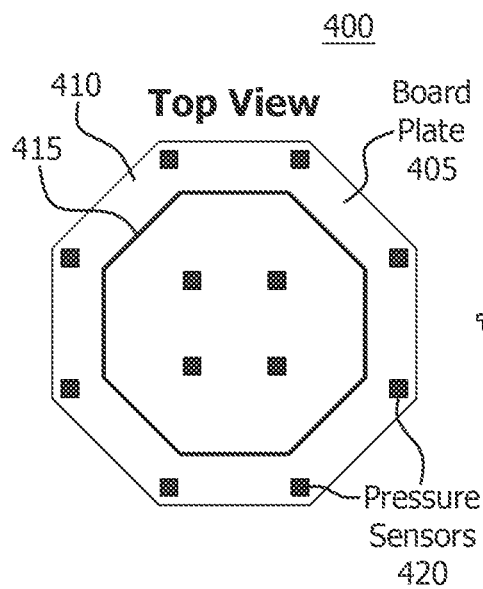
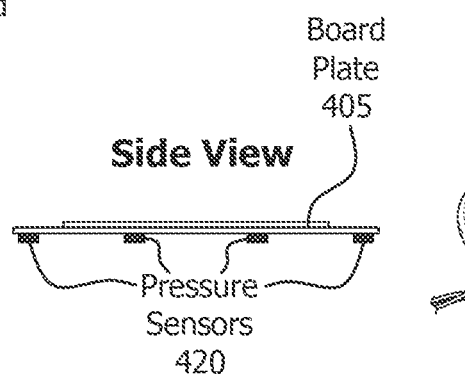
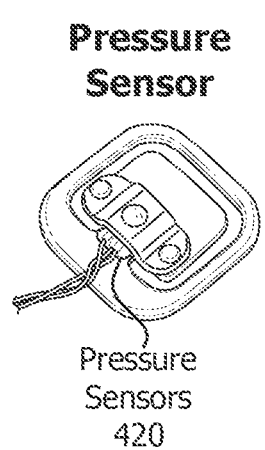
FIG. 4A
FIG. 4B
FIG. 4C

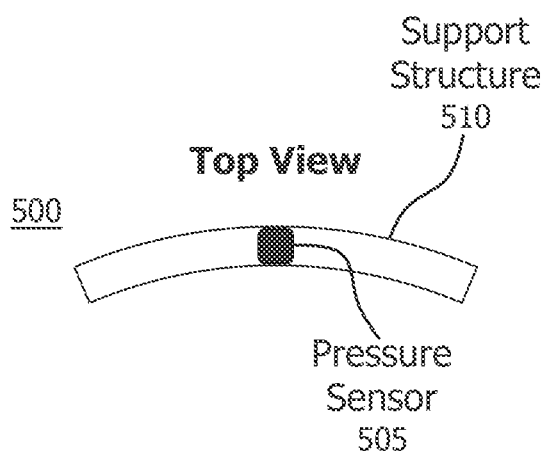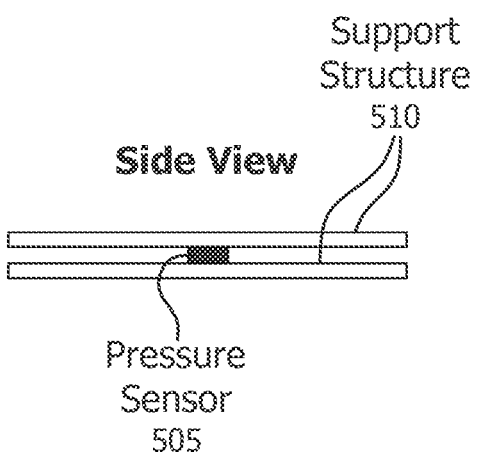
FIG. 5A
FIG. 5B
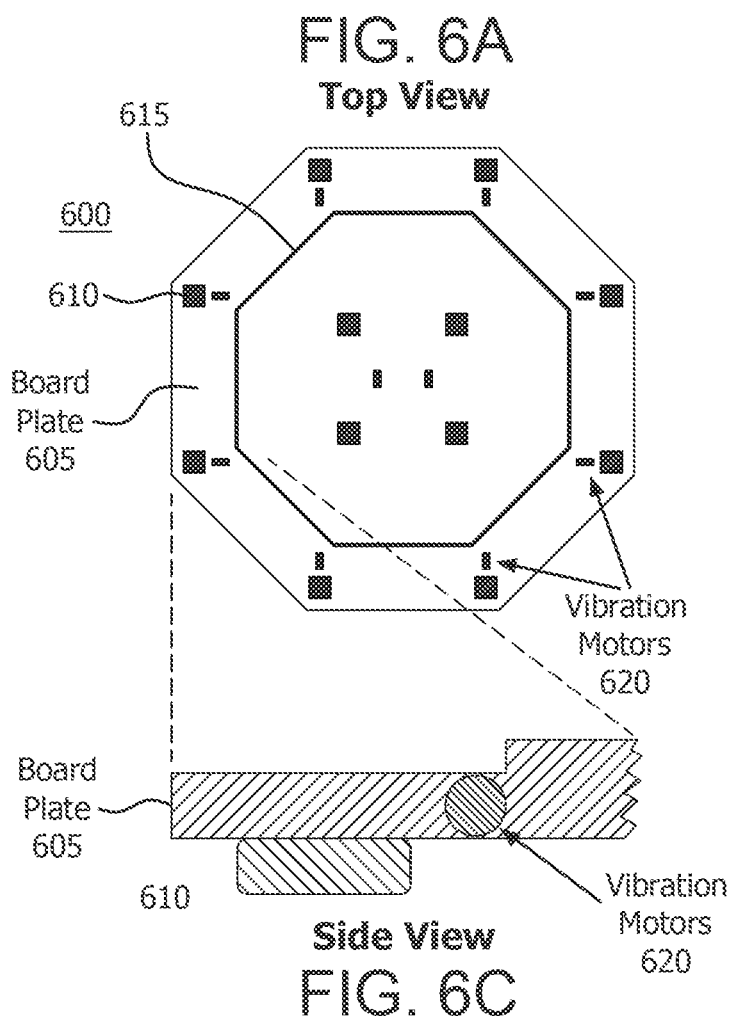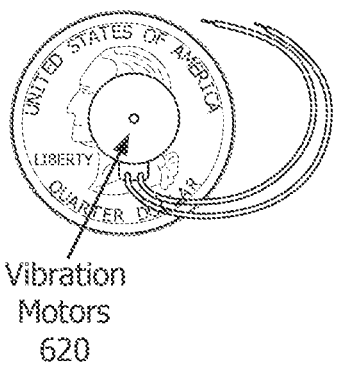
FIG. 6A
Top View
FIG. 6B
Vibration Motor vs. a US Quarter
FIG. 6C
Side View

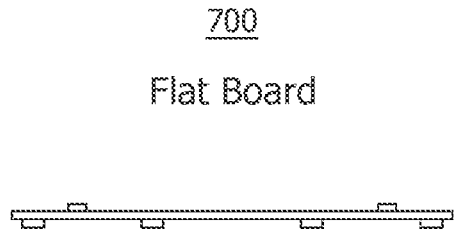
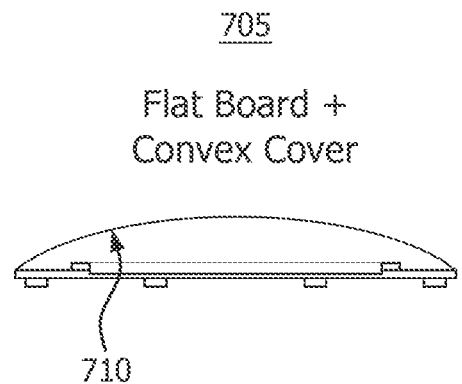
FIG. 7A
FIG. 7B
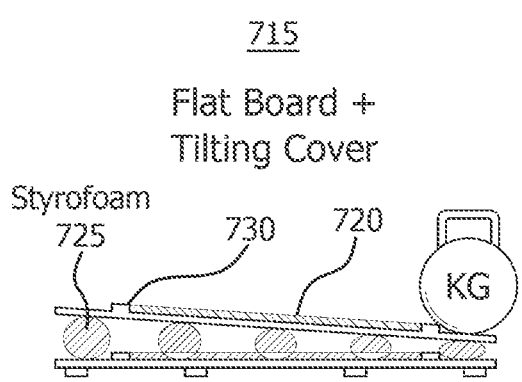
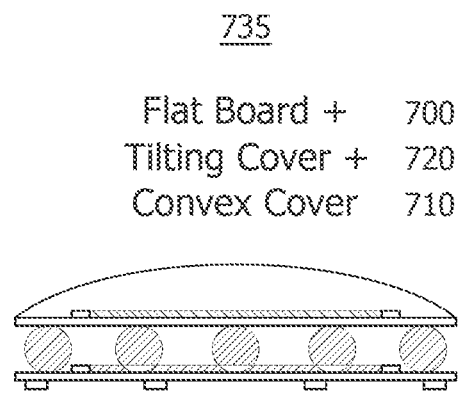
FIG. 7C
FIG. 7D

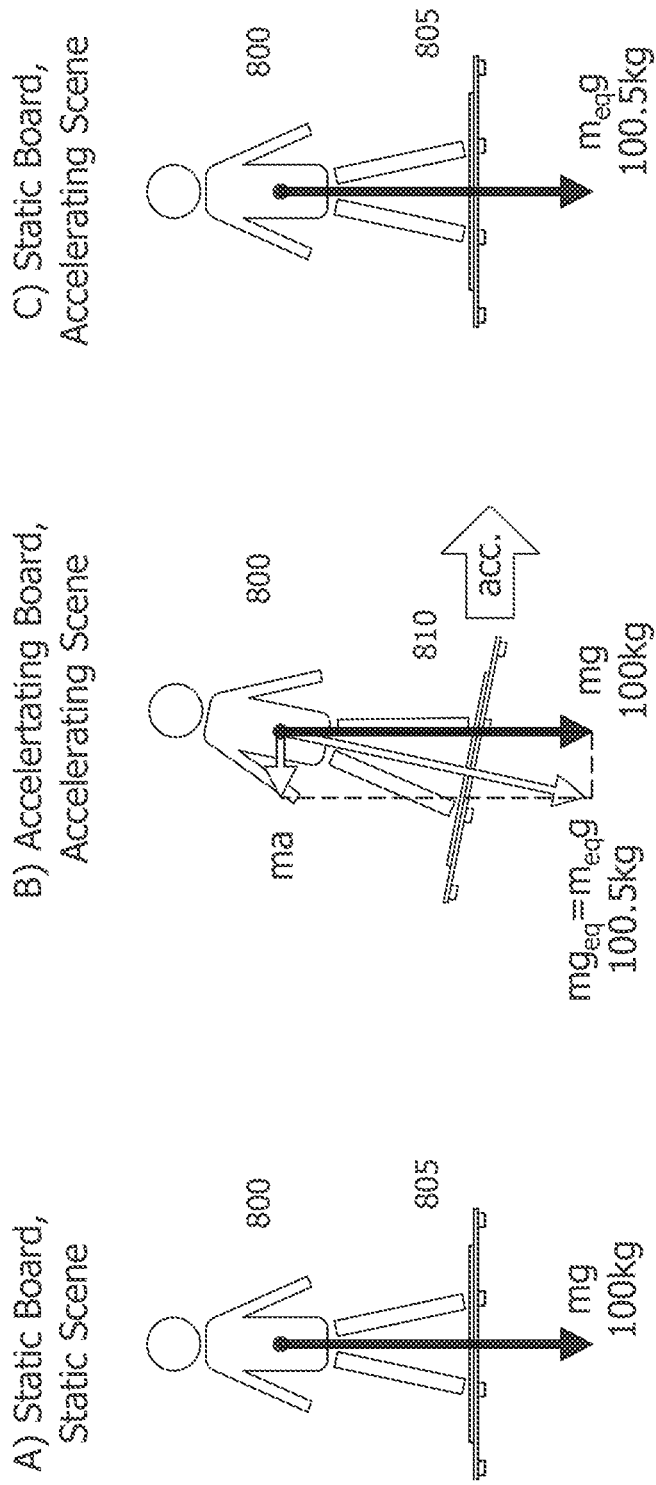

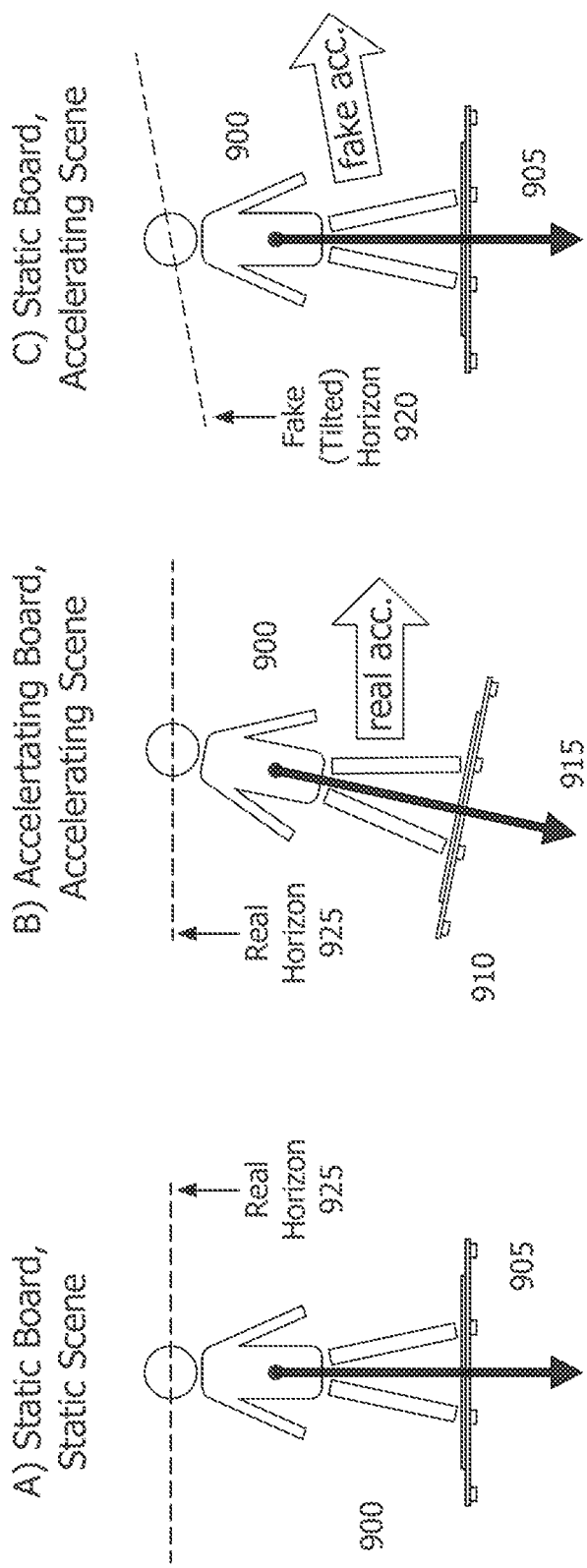

METHOD, APPARATUS AND SYSTEM FOR MITIGATING MOTION SICKNESS IN A VIRTUAL REALITY ENVIRONMENT

CROSS REFERENCE TO RELATED APPLICATION

This application claims the benefit of U.S. Provisional Application No. 62/558,620, filed Sep. 14, 2017, which is incorporated by reference as if fully set forth.

BACKGROUND

Virtual Reality (VR) is an emerging field which provides a user to be immersed in an environment without physically being there. An issue with VII technology is that the user may experience motion sickness resulting from the virtual and physical dichotomy.

BRIEF DESCRIPTION OF THE DRAWINGS

A more detailed understanding can be had from the following description, given by way of example in conjunction with the accompanying drawings wherein:

FIGS. 3A-3C are illustrative block diagrams of a VR controller board in accordance with certain implementations;

FIGS. 4A-4C are illustrative block diagrams of a VII controller board in accordance with certain implementations;

FIGS. 5A-5B are illustrative block diagrams of a VR controller board in accordance with certain implementations;

FIGS. 6A-6C are illustrative block diagrams of a VII controller board in accordance with certain implementations;

FIGS. 7A-7D are illustrative block diagrams of a VR controller board in accordance with certain implementations;

FIGS. 8A-8C are illustrative block diagrams of a VR controller board in accordance with certain implementations;

FIGS. 9A-9C are illustrative block diagrams of a VR controller board in accordance with certain implementations.

DETAILED DESCRIPTION

Figure 1:
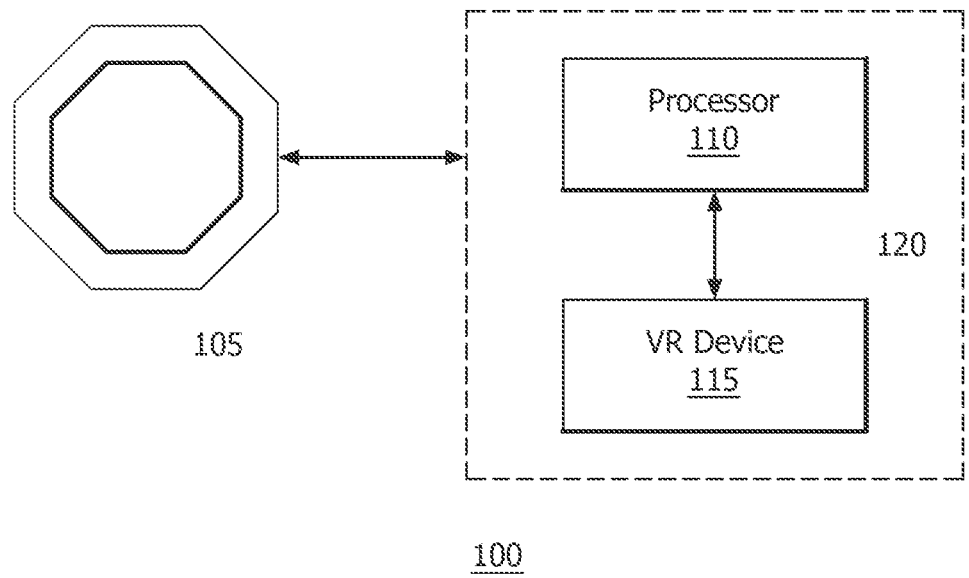
FIG. 1 is a system for providing virtual reality (VR) in accordance with certain implementations.

Described herein are a method, system and apparatus for mitigating motion sickness in a virtual reality (VR) environment. In an implementation, the system and apparatus can include a VII controller board, a processor and a VR headset. In an implementation, the processor and VR headset are an integrated device. In general, the method includes capturing measurements using the VII controller board. The measurements are indicative of user directional movements in a physical environment relative to the VR environment. In an implementation, the measurements relate to changes in a location of a center of mass of the user relative to the VR controller board. The processor uses the measurements to determine predetermined actions in the VR environment. For example, the predetermined action can be a virtual horizon tilting necessitated by user movements in the physical environment. The predetermined actions are then executed in the VII environment nearly simultaneous with the user directional movements in the physical environment.

As currently understood, motion sickness phenomenon is an evolutionary mechanism, designed to protect humans against poisoning. According to this theory, when humans eat poisoned food, (e.g., spoiled food, poison berries, poison mushrooms, etc.), due to the body's reaction to the poisoning, the distribution of fluids in the body would change. Specifically the fluid inside the inner ear, (which maybe functionally thought of as a gyroscope), would become more viscous. This would cause the inner ear to "report" improper/incorrect rotational and/or linear acceleration to the brain. The brain is capable of detecting this situation by noticing a significant discrepancy between perceived acceleration according to the vision system, and the perceived acceleration according to the inertial measurements (i.e., the inner ear). When such a discrepancy is detected, the brain would signal the body to expel the potentially poisonous food (i.e., to vomit), causing what we call "motion sickness" or "sea sickness". The terminology resulted from the fact that motion sickness happens when a person travels on a ship, and when he/she is inside the hull of a ship, visually the hull is static, but inertially the hull is moving (together with the rest of the ship), thus creating the aforementioned discrepancy and the feeling of nausea.

Given the above understanding, motion sickness can be avoided by matching the visual cues to inertial sensation. To achieve this precisely, one has to actually be moving in space. Fortunately, the inner ear is a very imprecise gyroscope/accelerometer, and therefore it is possible to fool the inner ear, giving the impression of a significant motion without actually moving that much.

A method for fooling the inner can be implemented by observing or incorporating at least some of the rules stated herein below. The precision of perception of vertical acceleration (Z) is very poor, and therefore vertical acceleration causes the least amount of motion sickness and is the easiest to "fool". The lateral (X-Y) acceleration is more precise than the vertical acceleration, but not appreciably so. In order to efficiently fool the brain, the actual acceleration has to start at the same time as the viewed acceleration, the actual acceleration has to be in the same direction as the viewed acceleration, and if there is no actual acceleration, then there should not be viewed acceleration and vice versa. The viewed acceleration can be two or even three times the actual acceleration without the brain realizing that something is incorrect (i.e. without causing nausea). The rotational acceleration is the most precise and is the hardest to fool. The best way to deal with it is to make sure that the viewed rotational acceleration is always small. That is, perform very gradual rotations.

In general and as further described herein, the VR controller board is implemented to match the time of the physical movement with the moment of the viewed motion in the VR world. In order to make the VR controller board move, the user has to either step, or otherwise transfer weight in the desired direction, and to achieve that the user has to be physically moving in the real world and that ensures that movement in the physical and simulated worlds occurs simultaneously, and in the same direction.

FIG. 1 is a system 100 for providing virtual reality (VR) in accordance with certain implementations. System 100 includes a VR controller board 105 connected to or in communication (collectively "connected to")) with a processor 110, which in turn in connected to a VR device 115. The term "connected to" can refer to wired, optical, wireless or any other communication method and any combinations thereof. Processor 110 can be, for example, a computer, a gaming device, a handheld device, a set-top box, a television, a mobile phone, a tablet computer or any device capable of or configured to accept input from VR controller board 105 as described herein. VR device 115 can be, for example, a VR headset, a gaming device, a handheld device, a mobile phone, a tablet computer or any device capable of or configured to accept input from processor 110 as described herein. In an implementation, processor 110 and VR device 115 are an integrated device 120.

VR controller board 105 is a man-machine interface that can be used with VR and other applicable technologies and applications. It mitigates the effects of the motion sickness, which is currently considered to be one of the biggest problems in VR. VR controller board 105 provides the user with a greater freedom of motion in a virtual world without the user suffering from the effects of motion sickness. For example, VR controller board 105 enables virtual travel and social virtual travel (travelling together with friends) without having to contend with motion sickness.

VR controller board 105 enables the user to experience an unprecedented level of VR immersion in terms of presence and flight, for example. It makes the user feel like he/she is actually "flying" in the simulated world. In contrast to existing methods of combating motion sickness, which act to detach the user from the immersive experience, VR controller board 105 maximizes the immersion.

Figure 2:
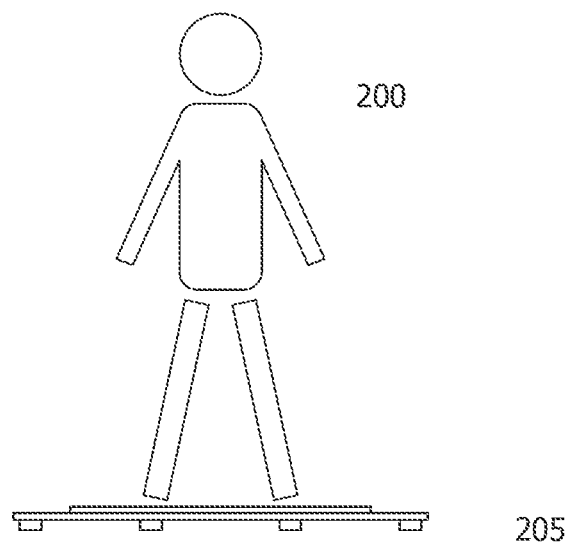
FIG. 2 is an illustrative diagram of a virtual reality (VR) controller board and a user positioned on the VR controller board in accordance with certain implementations.

In an implementation, VR controller board 105 is a pressure-sensitive pad that can detect the weight of the person standing on it, as well as the location of the user's center of mass. FIG. 2 illustrates a user 200 positioned on a VR controller board 205 in accordance with an implementation. The weight can be used to determine a variety of parameters or indicators including, but not limited to, vertical thrust and/or vertical movement in a simulated environment, audio feedback, haptic feedback and the like.

Operationally, with respect to FIGS. 1 and 2, a user steps or transfers weight on VR controller board 105 or 205 in a desired direction to control the virtual board's speed and acceleration in the horizontal (X-Y) plane. VR controller board 105 collects the measurements as described herein for processing by processor 110, for example. Processor 110 uses the measurements to cause a virtual board to move and adjust the virtual environment in VR device 115 accordingly.

Yaw (rotation around a vertical axis) can be similarly implemented depending on the type of VII simulation. In an implementation, if the flying experience is a room-scale experience, such as a system like Vive® VR, then the X-Y motion is sufficient, and the rotation (yaw) can be achieved by simply changing orientation by stepping on VR controller board 105 to face in different directions.

In an implementation, if the VR system is not room scale (like Oculus® VR), and it is important to (mostly) be facing a tracking camera positioned in front of user 200, the modeling of the virtual board incorporates physics features that are similar to a plane, skis, snowboard, yacht and the like. At low speeds (moving relatively slowly in virtual world), the virtual board can move freely both right and left and forward and backward. At higher forward speeds, transferring the weight (e.g. stepping) on the physical board to the right causes the virtual board to tilt and yaw right, just like a plane would. This creates a very pleasant and immersive perception of speed and flight.

Vertical movement and flying can also be implemented using VII controller board 105. In an implementation, additional controllers can be used. In an implementation, the virtual representation of the board has a "springiness" in the vertical direction. When initially stepping on VR controller board 105, the virtual board will "yield" a little downwards, but then gradually compensate and return to the initial position. As noted, this is all happening in the simulated world as VR controller board 105 does not "yield" vertically, does not tilt (unless a tilting add-on is used as described herein) and does not move horizontally. Stepping onto the virtual board in this case is similar to stepping onto a drone-powered platform (e.g. quadcopter). Such a platform will initially yield under the added weight, and then turn to its original position due to the drone compensating for the added weight. In an implementation, it is also possible to cause the virtual board to rock/swing up and down by "pumping" a little on VII controller board 105 upwards and downwards ("pumping" is not exactly jumping up and down; it is more like rhythmical bending and straightening of the knees). In an implementation, the simulated virtual board has a natural resonant frequency, and when the rhythmic "pumping" up and down roughly matches that frequency, the amplitude of the vertical rocking of the virtual board will increase. For example, the controlling motion might be similar to standing and flapping your hands "like a bird" while helping with your legs/knees.

The simulated virtual board acts essentially like an oscillator, and by rocking it up and down, energy is pumped into this oscillator. When the "pumping" stops, the simulated virtual board's rocking decays back to original position. The energy of this virtual oscillator is then used as a vertical thrust control. To fly upwards in the simulated world, the user needs to "start pumping" (modulating) up/down on VII controller board 105, and to fly downwards in the simulated world, the user simply needs to stop pumping on VR controller board 105. The user can stay at a specific height above the ground in the simulated virtual world by "pumping" at a constant rhythm/amplitude on VII controller board 105.

The above vertical control scheme is very intuitive and it is very easy for the user to control his/her height in the virtual world as well as control his/her ascent and descent in the virtual world. Also, if the user is not intending to fly up/down, and simply wants to navigate in the horizontal plane, no (or very little) "false detection" happens. The vertical and horizontal controls are therefore nicely separated and can be applied independently or in unison, as desired. For example, in the virtual world, the user can tilt right/left or accelerate/decelerate, while also controlling his/her vertical position. In addition, such a method of control gives the user immersive perception of flight and the perception of actually "making huge vertical leaps in the virtual world" while doing it.

VR controller board 105 or 205 can be implemented in a variety of shapes including, but not limited to, round, octagon, rectangular, and the like. FIGS. 3A-3C illustrate a top view and two side views of a VR controller board 300 in an octagonal shape. In this implementation, VII controller board 300 has 8 pressure sensors 315 that act as 8 support points at an outer rim 310 of a board plate 315. Implementation in other shapes can require different sensor and support configurations, all of which are within the scope of the claims presented herein. As shown in FIGS. 3A-3C, VR controller board 300 includes a tactile rail 325 on a top surface 320 of board plate 315. Tactile rail 325 is a protrusion on VR controller board 300 that assists a user to be aware of his/her position on top surface 320 of VII controller board 300 in a non-obtrusive way. The user can step anywhere on VII controller board 300 and tactile rail 325 provides instant awareness and/or situational feedback. In an implementation, top surface 320 of VR controller board 300 can have no positional queues at all (e.g. be completely flat), and the positional awareness would be achieved by VII visualization. In an implementation, the VII experience causes the user to naturally stay on VR controller board 300 and not step off of VR controller board 300 unintentionally. Other techniques can be used to inform the user of the user's location or position on VR controller board 300.

In an implementation, a top part 330 of VR controller board 300 can have a convex shape. This also provides the user a method for being aware of his/her location on VII controller board 300, as well as improving immersion. The convex shape is illustrative and other shapes can be used for top part 330, such as, but not limited to, concave and/or other (more complex) shapes. As illustrated herein, top part 330 can be implemented as a cover for VR controller board 300.

Operationally, a user steps or transfers weight on VR controller board 300 in a desired direction to control the board speed and acceleration in the horizontal (X-Y) plane in the VII environment as described herein.

FIGS. 4A-4C provide another illustration of a VR controller board 400. As described herein, VR controller board 400 includes a board plate 405. A tactile rail 415 is implemented on a top surface 410 of board plate 405. In an implementation, VR controller board 400 includes pressure sensors 420. For example VR controller board 400 can use 12 pressure sensors 420, each rated at 50 lbs. The number (and type) of pressure sensors 420 can be altered based upon the shape, size and material of VR controller board 400.

The number (and type) of pressure sensors 420 can reliably measure the center of gravity only if the center of mass is applied inside a convex hull of the pressure sensor 420 locations, where the convex hull or convex envelope of a set X of points in a Euclidean plane or in a Euclidean space (or, more generally, in an affine space over the reals) is the smallest convex shape that contains X. Moreover, the density of pressure sensors 420 needs to be sufficient so that VR controller board 400 does not touch a floor during bending or flexing as such touching of the floor would bypass pressure sensor measurements.

As stated above, the configuration of VR controller board 400 is such that no part of the weight bypasses pressure sensors 420. This means that pressure sensors 420 are the only support points. If VR controller board 400 was to bend and some part of VR controller board 400 was to touch the floor, the data will not be accurate. Also, the data is only accurate when the center of mass is inside the convex hull defined by pressure sensors 420 placement. When the center of mass is outside the convex hull of the support points represented by pressure sensors 420, the structure is no longer stable and VR controller board 400 may tip over, (this can be corrected by proper selection and positioning of pressure sensors 420). The center of mass in question is the combined center of mass of a user plus VR controller board 400. If the user's center of mass is a little bit outside the convex hull, the total center of mass may still be inside of the convex hull due to the weight of VR controller board 400. Consequently, VR controller board 400 operates independently of the evenness of the floor, works reliably and reports the correct total weight and the correct center of mass in most floor conditions. For example, VR controller board 400 will work reliably on soft surfaces (like a carpet), where it is practically impossible to require a uniform distribution of weight among pressure sensors 420.

FIGS. 5A and 5B illustrate sectional top and side views of a VR controller board 500 including a pressure sensor 505, in accordance with an implementation. In this implementation, pressure sensor 505 has a support structure 510 which is wider than a single pressure sensor 505. This alleviates the restrictions on the shape of VR controller board 500 but will reduce the directional accuracy of the detected center of mass.

FIGS. 6A-6C illustrate a VR controller board 600 which employs haptic feedback. VII controller board 600 includes a board plate 605, pressure sensors 610, a tactile rail 615 on board plate 605 and vibration motors 620. Vibration motors 620 are embedded in board plate 605 of VR controller board 600 to provide haptic feedback in VR controller board 600. In an implementation, vibration motors 620 can use 10 "coin" vibration motors as shown in FIG. 6B. The number (and type) of vibration motors can vary as per the haptic feedback effect desired.

Haptic feedback is provided via vibration motors 620 to further convince our brain that VII controller board 600 is actually tilting when moving around. In an implementation, the tilting is expressed by relating the amount of vibration proportional to the angular speed of the virtual representation of VR controller board 600. In an implementation, the tilting is expressed by relating the amount of vibration proportional to the tilt angle of the virtual representation of VR controller board 600. In an implementation, other methods of relating the vibration to simulated virtual board movement are possible. In an implementation, vibration can be used for other haptic events as well. In addition, haptic feedback can be used to express the change of terrain (going over smooth surface or rocky road), and to express jumps/falls/explosions and the like.

In an implementation, additional types of haptic feedback can be included, but are not limited to, knocking actuators, linear resonant actuators (LRAs) and the like. In an implementation, more than one type of haptic actuators can be present in VR controller board 600 at the same time. In an implementation, the VII controller board 600 can be divided into segments, and each segment can provide independent haptic feedback.

FIGS. 7A-7D illustrate implementations for VR controller boards. FIG. 7A illustrates a VII controller board 700 which is generally flat and without moving parts. In an implementation, VII controller board 700 can be made as a thin pressure-sensitive pad. FIG. 7B illustrates a VR controller board 705 which can include VR controller board 700 with a convex cover or dome 710 for improving immersion. In an implementation, a VR controller board can include a concave cover and/or other shapes. FIG. 7C illustrates a VR controller board 715 which includes VR controller board 700 with a tilting cover 720, which allows the platform to tilt for improving immersion. In an implementation, tilting cover 720 can be implemented using for example styrofoam 725 between VR controller board 700 and tilting cover 720. In an implementation, other materials can be used instead of styrofoam 725 to permit the tilting effect. In this implementation, a tactile rail 730 is replicated on tilting cover 720 as a user would stand on tilting cover 720. In this implementation, vibration motors can be replicated on tilting cover 720 as well because the soft styrofoam dampens mechanical vibrations. In an implementation, tilting 720 can be a motorized tilting cover for greater immersion. In an implementation, VR controller board 715 can include a thrusting (up/down) cover for more advanced haptics. In an implementation, VR controller board 715 can include a springy cover for advanced interaction. FIG. 7D illustrates a VR controller board 735 which includes VR controller board 700 with a convex cover 710, and a tilting cover 720 for improving immersion. In an implementation, VR controller board can include any combination of the above implementations.

As stated herein, the VR controller board is implemented to match the time of the physical movement with the moment of movement in the VR world. In order to make the VR controller board move, the user has to either step, or transfer weight in the desired direction and that ensures that movement in the physical and simulated worlds occurs simultaneously, and in the same direction. In effect, the VR controller board attempts to convince the brain that what the user "sees" in VR and what the user "feels" matches up. This is illustrated in FIGS. 8A-8C with respect to inertial perception and in FIGS. 9A-9C with respect to horizon tilting.

FIGS. 8A-8C illustrate the user's inertial perception. The parameters listed in Table 1 are illustrative.

TABLE 1

| | |
|---|---|
| mass = 100 kg | mass of the person |
| g = 10.0 m/s$^2$ | freefall acceleration |
| a = 1.0 m/s$^2$ | lateral board acceleration |
| $g_{eq}$ = sqrt (g$^2$ + a$^2$) = 10.05 m/s$^2$ | equivalent freefall acceleration |
| $m_{eq}$ = m*$g_{eq}$/g = 100.5 kg | equivalent mass of the person |

In FIG. 8A, a user 800 stands straight on a static board 805, and "sees" in VR that he/she is standing on a static virtual board. In FIG. 8B, user 800 stands straight on a physically accelerating board 810 that is properly reclined (such that the vector of force is perpendicular to the board), and "sees" in VR that he/she is standing on an accelerating virtual board as well. In FIG. 8C, user 800 stands on a static board 805, but "sees" in VR that he/she is standing on a reclined and accelerating virtual board.

In the cases illustrated in FIGS. 8A and 8B, the physical reality matches perfectly to the observed virtual reality. In FIG. 8A, user 800 "feels" that he/she weighs 100 kg, and in FIG. 8B (board 810 is accelerating laterally at 1.0 m/s$^2$), user 800 "feels" that he/she weighs 100.5 kg. For the cases in FIGS. 8A and 8B, user 800 "feels" a force that is pushing him/her perpendicularly to board 805 and 810, respectively, but this force is different in each case, i.e., 100 kg vs 100.5 kg.

In the case illustrated in FIG. 8C, the physical reality does not exactly match the observed reality. User 800 should have been feeling the weight of 100.5 kg but instead he/she feels only 100 kg. Our brain, however, is incapable of detecting such a small difference in weight. Therefore, the brain can be "fooled" into believing that the observed reality indeed matches the physical sensations, and thus user 800 actually perceives him/her-self standing on an accelerating virtual board, while in fact the physical board is completely static.

The challenge in VR is to transition from the state of FIG. 8A to the state of FIG. 8C in a believable way. This is illustrated with respect to FIGS. 9A-9C by implementing horizon tilting.

FIG. 9A shows a user 900 standing straight on a static board 905 and FIG. 9B shows user 900 standing straight on an accelerating board 910 that is properly reclined such that the equivalent gravity vector is perpendicular to the board as shown by arrow 915. When user 900 is accelerating in physical reality, arrow 915 is no longer perpendicular to the horizon. Therefore, in order to fool user 900's brain into believing in the fake acceleration in VR, a VII horizon 920 (and the rest of the scene with it) needs to be tilted accordingly as shown in FIG. 9C in contrast to a real horizon 925 as shown in FIGS. 9A and 9B. In VR, this can be achieved by offsetting the view camera angle relative to detected real horizon 925.

In an implementation, wind resistance can be similarly simulated. If we are being physically correct, then in the case that the virtual board is in constant-speed motion (no longer accelerating), the VR horizon angle should once again match the real physical horizon, and the board in VII should appear to be aligned perpendicularly to it. In practice, however, it feels more natural if the board in VR is still tilted in the direction of motion (and the horizon will therefore also still be tilted). This matches the effect of compensating for wind resistance, i.e., leaning forward against the wind. This creates a better sense of immersion, which is further improved once wind sound effects are added to the simulation.

In an implementation, the VII controller board can also be made as a thin, flexible (foldable/rollable) pressure sensitive pad.

In an implementation, the VR controller board functionality can be implemented using shoes which the user would put on. The shoes can have built-in pressure sensors, in addition to a positioning system that would be able to tell where each foot is located on the floor, so that it would be possible to calculate the location of center of mass relative to the floor. These shoes can also have haptic feedback actuators built into them.

In an implementation, a depth camera can be used (mounted in front of the user for example) to reconstruct the pose of the user, including location and size of all the limbs, and calculate (estimate) the center of mass of the person from that information. The depth camera would negate the need for the VR controller board and/or shoes (except for the haptic feedback). In this case all the movement controls (horizon tilting, plane-like yaw turning, flying by "pumping", etc.) described herein are applicable.

In an implementation, the VR controller board can have built-in tracking sensors (like upward-looking cameras, upward-looking depth camera, thermal imaging sensor, infrared camera and the like) that would enable the processor to tell where each foot is located relative to the board, and reconstruct the human pose for VII visualization, games, and social experiences. This will allow the visualization of the user while in VR, either for looking at his/her own body, or while looking at other users. This would also enable the use of additional gestures like kicking an object with a foot (a football etc.) and other gestures.

In an implementation, the VII controller board can have a built-in positioning sensor (like "Vive tracker"), to allow the VR system to correctly position the VII controller board within the virtual space. Such sensor can be detachable because the VR controller board is static and needs to be positioned (calibrated) only once, (after the calibration the sensor can be removed). An existing VR motion controller (like the ones provided with Vive and Oculus solutions) can play the role of such one-time calibration sensors.

In an implementation, a chair can be placed onto the VR controller board, and the user can lean right/left/forth/back while sitting in the chair (instead of standing) and control movement that way.

In an implementation, the VR controller board can use an optional safety rail around the VR controller board, to prevent beginner users from tipping over or falling. For example, the optional safety rail can be at waist height level.

In an implementation, the VR controller board can be used as a controller for other (non-VR) experiences such as non-VR games and the like. In an implementation, the VR controller board can be used as a floor scale. In an implementation, the VII controller board can be used to improve balance and timing of weight transfer. This can improve the dancing skills of people, martial arts skills or help recuperate after an accident etc.

The VR controller board enables traveling in the simulated world without getting motion sickness, and without breaking the immersion (unlike the currently used methods). The VR controller board is a static system, and is easily implementable.

Although discussed in terms of virtual reality applications, the specification and claims are applicable to augmented reality environments.

Figure 10:
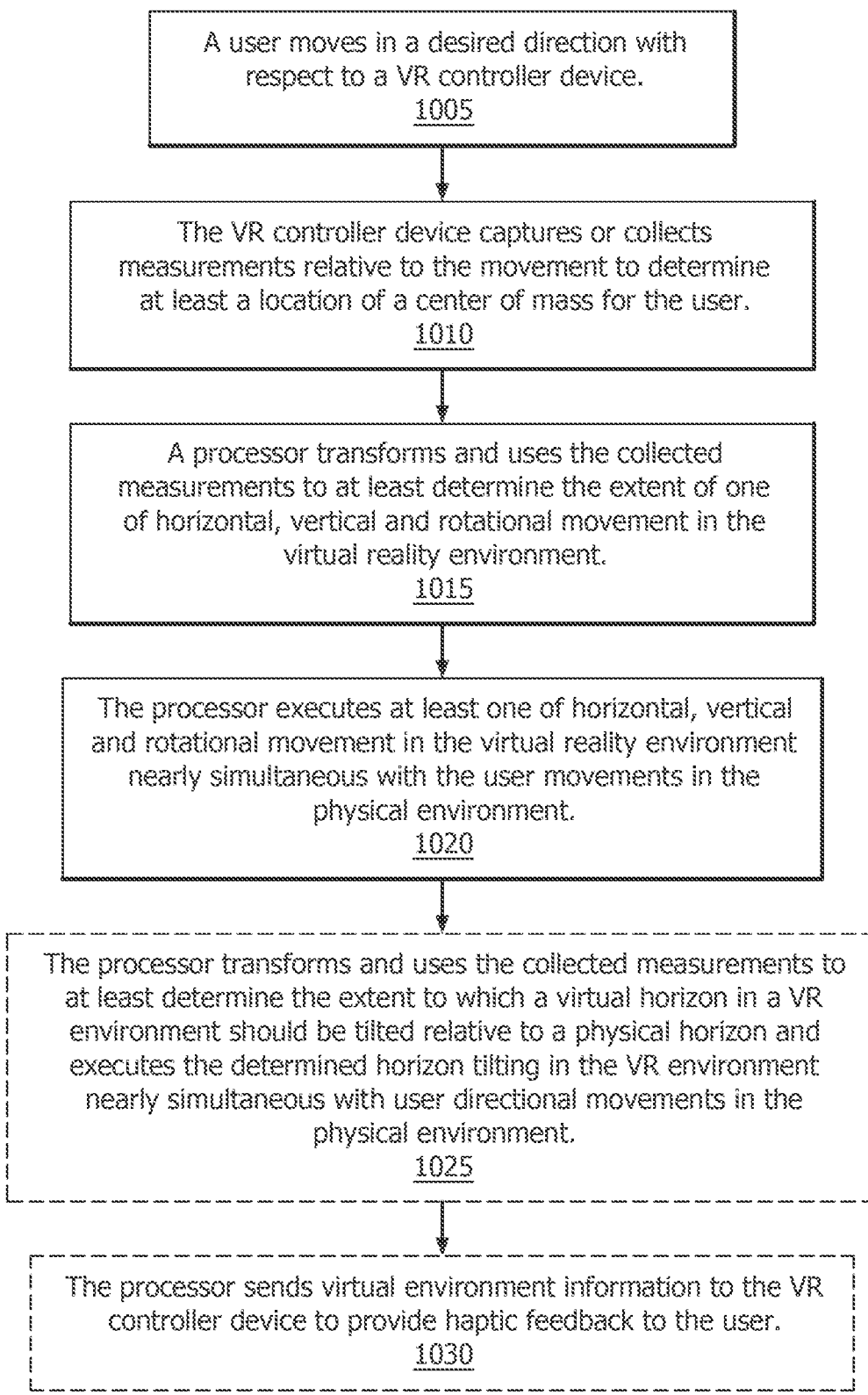
FIG. 10 is an example flowchart of a method for mitigating motion sickness in a virtual reality environment in accordance with certain implementations.

FIG. 10 is an example flowchart 1000 of a method for mitigating motion sickness in a virtual reality environment in accordance with certain implementations. A user moves in a desired direction with respect to a VR controller device (step 1005). The VR controller device captures or collects measurements relative to the movement to determine at least a location of a center of mass for the user (step 1010). In an implementation, the VR controller device captures or collects measurements relative to the movement to determine at least a total mass. A processor transforms and uses the collected measurements to at least determine the extent of one of horizontal, vertical and rotational movement in the virtual reality environment (step 1015). The processor executes at least one of horizontal, vertical and rotational movement in the virtual reality environment nearly simultaneous with the user movements in the physical environment (step 1020). In an implementation, the processor transforms and uses the collected measurements to at least determine the extent to which a virtual horizon in a VR environment should be tilted relative to a physical horizon and executes the determined horizon tilting in the VR environment nearly simultaneous with user directional movements in the physical environment (step 1025). In an implementation, the processor sends virtual environment information to the VR controller device to provide haptic feedback to the user (step 1030).

In general, a method for mitigating motion sickness using a processor. The method includes receiving at least a location of a center of mass of a user, where the center of mass indicative of user movements in a physical environment relative to a virtual reality environment. The method further includes determining based on at least the location of the center of mass an extent of horizontal, vertical and rotational movement in the virtual reality environment and causing at least one of horizontal, vertical and rotational movement in the virtual reality environment nearly simultaneous with the user movements in the physical environment. In an implementation, the method further includes determining based on at least the location of the center of mass an extent to which a virtual horizon needs to be tilted relative to a physical horizon and causing virtual horizon tilting in the virtual reality environment nearly simultaneous with the user movements in the physical environment when the user movements necessitate the virtual horizon tilting. In an implementation, the method further includes sending haptic feedback commands for execution on a virtual reality controller device. In an implementation, a level of haptic feedback is proportional to an angular speed of a virtual representation of the virtual reality controller device. In an implementation, a level of haptic feedback is proportional to a tilt angle of a virtual representation of the virtual reality controller device. In an implementation, a level of haptic feedback is reflective of a type of terrain being traversed by a virtual representation of the virtual reality controller device. In an implementation, the method further includes receiving at least a weight of the user to determine at least one parameter or indicator.

In general, a virtual reality device includes a processor configured to receive at least a location of a center of mass of a user, where the center of mass indicative of user movements in a physical environment relative to a virtual reality environment. The processor further configured to determine based on at least the location of the center of mass an extent of horizontal, vertical and rotational movement in the virtual reality environment and cause at least one of horizontal, vertical and rotational movement in the virtual reality environment nearly simultaneous with the user movements in the physical environment. In an implementation, the processor is further configured to determine based on at least the location of the center of mass an extent to which a virtual horizon needs to be tilted relative to a physical horizon and cause virtual horizon tilting in the virtual reality environment nearly simultaneous with the user movements in the physical environment when the user movements necessitate the virtual horizon tilting. In an implementation, the processor is further configured to provide haptic feedback commands to the virtual reality controller. In an implementation, a level of haptic feedback is proportional to an angular speed of a virtual representation of the virtual reality controller. In an implementation, a level of haptic feedback is proportional to a tilt angle of a virtual representation of the virtual reality controller. In an implementation, a level of haptic feedback is reflective of a type of terrain being traversed by a virtual representation of the virtual reality controller.

In general, a virtual reality controller includes a platform and a plurality of pressure sensors attached to the platform. The pressure sensors detect at least a location of a center of mass of a user, where the center of mass indicative of user movements in a physical environment relative to a virtual reality environment. The virtual reality controller is configured to send the at least the location of the center of mass to cause at least one of horizontal, vertical and rotational movement in the virtual reality environment nearly simultaneous with the user movements in the physical environment. In an implementation, where the at least the location of the center of mass is further indicative of an extent to which a virtual horizon needs to be tilted relative to a physical horizon and the sending of the at least the location of the center of mass causes virtual horizon tilting in the virtual reality environment nearly simultaneous with the user movements in the physical environment when the user movements necessitate the virtual horizon tilting. In an implementation, the virtual reality controller includes a support structure associated with each of the plurality of pressure sensors. In an implementation, the virtual reality controller is configured to receive haptic feedback commands, and further includes vibration motors attached to the platform for providing haptic feedback to the user. In an implementation, a level of haptic feedback is proportional to an angular speed of a virtual representation of the virtual reality controller. In an implementation, a level of haptic feedback is proportional to a tilt angle of a virtual representation of the virtual reality controller. In an implementation, a level of haptic feedback is reflective of a type of terrain being traversed by a virtual representation of the virtual reality controller. In an implementation, the platform includes a tactile rail for indicating a position of the user on the platform. In an implementation, the virtual reality controller further includes a convex cover for indicating a position of the user on the platform. In an implementation, the virtual reality controller further includes a tilting cover. In an implementation, the virtual reality controller further includes upward looking pose estimation sensors.

It should be understood that many variations are possible based on the disclosure herein. Although features and elements are described above in particular combinations, each feature or element can be used alone without the other features and elements or in various combinations with or without other features and elements.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for mitigating motion sickness using a processor, the method comprising:
    determining a location of a center of mass of a user in a physical environment based on measurements from a plurality of pressure sensors;
    determining based on at least the location of the center of mass, an extent of motion in a virtual reality environment, wherein the extent of motion includes at least one of horizontal, vertical or rotational movement in the virtual reality environment;
    based on the location of the center of mass and the extent of motion in the virtual reality environment, determining a degree to which a virtual horizon is to be tilted in order to generate virtual acceleration, the determined degree corresponding to an angle between the virtual horizon and a real horizon; and
    tilting the virtual horizon by the determined degree by offsetting a view camera angle in the virtual reality environment.

2. The method of claim 1, further comprising:
    sending haptic feedback commands for execution on a virtual reality controller device.

3. The method of claim 2, wherein a level of haptic feedback is proportional to an angular speed of a virtual representation of the virtual reality controller device.

4. The method of claim 2, wherein a level of haptic feedback is proportional to a tilt angle of a virtual representation of the virtual reality controller device.

5. The method of claim 2, wherein a level of haptic feedback is reflective of a type of terrain being traversed by a virtual representation of the virtual reality controller device.

6. The method of claim 1, further comprising:
    receiving at least a weight of the user to determine at least one parameter or indicator.

7. A virtual reality device comprising:
    a processor configured to:
        determining a location of a center of mass of a user in a physical environment based on measurements from a plurality of pressure sensors;
        determine based on at least the location of the center of mass an extent of motion in a virtual reality environment, wherein the extent of motion includes at least one of horizontal, vertical or rotational movement in the virtual reality environment;
        based on the location of the center of mass and the extent of motion in the virtual reality environment, determine a degree to which a virtual horizon is to be tilted in order to generate virtual acceleration, the determined degree corresponding to an angle between the virtual horizon and a real horizon; and
        tilt the virtual horizon by the determined degree, by offsetting a view camera angle in the virtual reality environment.

8. The virtual reality device of claim 7, wherein the processor is further configured to provide haptic feedback commands to the virtual reality controller.

9. The virtual reality device of claim 8, wherein a level of haptic feedback is proportional to an angular speed of a virtual representation of the virtual reality controller.

10. The virtual reality device of claim 8, wherein a level of haptic feedback is proportional to a tilt angle of a virtual representation of the virtual reality controller.

11. The virtual reality device of claim 8, wherein a level of haptic feedback is reflective of a type of terrain being traversed by a virtual representation of the virtual reality controller.

12. The virtual reality device of claim 8, wherein the processor is further configured to receive at least a weight of the user to determine at least one parameter or indicator.

13. A non-transitory computer readable medium including instructions, which when executed by a device having a processing capability, causing the device to execute instructions to perform operations for mitigating motion sickness comprising:
    determining a location of a center of mass of a user in a physical environment based on measurements from a plurality of pressure sensors;
    determining based on at least the location of the center of mass, an extent of motion in a virtual reality environment, wherein the extent of motion includes at least one of horizontal, vertical or rotational movement in the virtual reality environment;
    based on the location of the center of mass and the extent of motion in the virtual reality environment, determining a degree to which a virtual horizon is to be tilted in order to generate virtual acceleration, the determined degree corresponding to an angle between the virtual horizon and a real horizon; and tilting the virtual horizon by the determined degree by offsetting a view camera angle in the virtual reality environment.

14. The non-transitory computer readable medium of claim 13, further comprising instructions causing the device to execute instructions comprising:
sending haptic feedback commands for execution on a virtual reality controller device.

15. The non-transitory computer readable medium of claim 14, wherein a level of haptic feedback is proportional to an angular speed of a virtual representation of the virtual reality controller device.

16. The non-transitory computer readable medium of claim 14, wherein a level of haptic feedback is proportional to a tilt angle of a virtual representation of the virtual reality controller device.

17. The non-transitory computer readable medium of claim 14, wherein a level of haptic feedback is reflective of a type of terrain being traversed by a virtual representation of the virtual reality controller device.

18. The non-transitory computer readable medium of claim 13, further comprising instructions causing the device to execute instructions comprising:
receiving at least a weight of the user to determine at least one parameter or indicator.

19. The method of claim 1, wherein the virtual acceleration is acceleration in the virtual reality environment.

20. The virtual reality device of claim 7, wherein the virtual acceleration is acceleration in the virtual reality environment.

* * * * *